US010414686B2

(12) United States Patent
Debbage et al.

(10) Patent No.: US 10,414,686 B2
(45) Date of Patent: Sep. 17, 2019

(54) LUMINESCENT GLASS COMPOSITION

(71) Applicant: D. Swarovski KG, Wattens (AT)

(72) Inventors: Roy Debbage, Kematen In Tirol (AT); Rainer Haid, Roppen (AT); Helmut Judmaier, Kolsass (AT); Johannes Maier, Innsbruck (AT); Florian Meissl, Rum (AT); Gerold Sprachmann, Kolsassberg (AT)

(73) Assignee: D. Swarovski KG, Wattens (AT)

( * ) Notice: Subject to any disclaimer, the term of this patent is extended or adjusted under 35 U.S.C. 154(b) by 144 days.

(21) Appl. No.: 15/318,534

(22) PCT Filed: Aug. 24, 2015

(86) PCT No.: PCT/EP2015/069382
§ 371 (c)(1),
(2) Date: Dec. 13, 2016

(87) PCT Pub. No.: WO2016/030340
PCT Pub. Date: Mar. 3, 2016

(65) Prior Publication Data
US 2017/0166474 A1    Jun. 15, 2017

(30) Foreign Application Priority Data

Aug. 27, 2014 (EP) .................................... 14182551

(51) Int. Cl.
| | |
|---|---|
| *C03C 3/118* | (2006.01) |
| *C03C 3/095* | (2006.01) |
| *C03C 3/102* | (2006.01) |
| *C03C 3/15* | (2006.01) |
| *C03C 3/16* | (2006.01) |
| *C03C 4/00* | (2006.01) |
| *C03C 4/02* | (2006.01) |
| *C03C 4/12* | (2006.01) |
| *C03C 3/097* | (2006.01) |
| *C03C 3/108* | (2006.01) |
| *C09K 11/77* | (2006.01) |
| *G01N 21/64* | (2006.01) |
| *G01N 21/87* | (2006.01) |
| *A44C 17/00* | (2006.01) |

(52) U.S. Cl.
CPC ............ *C03C 3/118* (2013.01); *A44C 17/008* (2013.01); *C03C 3/095* (2013.01); *C03C 3/097* (2013.01); *C03C 3/102* (2013.01); *C03C 3/108* (2013.01); *C03C 3/15* (2013.01); *C03C 3/16* (2013.01); *C03C 4/0028* (2013.01); *C03C 4/02* (2013.01); *C03C 4/12* (2013.01); *C09K 11/778* (2013.01); *C09K 11/7742* (2013.01); *C09K 11/7782* (2013.01); *C09K 11/7792* (2013.01); *C09K 11/7797* (2013.01); *C09K 11/7798* (2013.01); *G01N 21/645* (2013.01); *G01N 21/87* (2013.01)

(58) Field of Classification Search
CPC ........... C03C 4/12; C03C 3/068; C03C 3/062; C03C 3/095; C03C 3/15; G01N 21/87; G01N 21/64; A44C 17/008; C09K 11/77; C09K 11/7728; C09K 11/7743; C09K 11/7756; C09K 11/7715; C09K 11/7766; C09K 11/7783
See application file for complete search history.

(56) References Cited

U.S. PATENT DOCUMENTS

| | | | |
|---|---|---|---|
| 3,855,144 A | 12/1974 | Barber et al. | |
| 5,516,227 A | 5/1996 | Kozak et al. | |
| 6,705,114 B2* | 3/2004 | Steiner | ................ A44C 17/008 63/14.9 |
| 7,256,398 B2* | 8/2007 | Ross | ...................... C03C 3/091 250/302 |
| 2005/0253113 A1 | 11/2005 | Letz et al. | |
| 2006/0037366 A1 | 2/2006 | Chen et al. | |
| 2008/0153068 A1 | 6/2008 | Kessler et al. | |
| 2010/0242540 A1* | 9/2010 | Swarovski | ........... A44C 17/001 63/26 |
| 2011/0189412 A1 | 8/2011 | Renard et al. | |

FOREIGN PATENT DOCUMENTS

| | | |
|---|---|---|
| CN | 101269910 A | 9/2008 |
| CN | 101843394 A | 9/2010 |
| CZ | 302723 B6 | 9/2011 |
| EP | 0 466 932 A1 | 1/1992 |
| EP | 0 738 243 B1 | 9/1998 |
| EP | 1 491 350 A2 | 12/2004 |
| EP | 1837312 A1 | 9/2007 |
| EP | 1725502 B1 | 9/2009 |
| RU | 2093617 C1 | 10/1997 |
| RU | 2207991 * | 7/2003 |
| RU | 2003137708 A | 6/2005 |
| RU | 2421710 C2 | 6/2011 |

(Continued)

OTHER PUBLICATIONS

Abstract for RU 2212380, Sep. 20, 2003.*
Abstract of European Patent, WO2011141461 A1, dated Nov. 17, 2011, 2 pages.
International Search Report for PCT/EP2015/069382, dated Jul. 1, 2016, 2 pages.
Search Report and Patent Examination Report; Russian Patent Application No. 2016149800; Rospatent; dated Feb. 21, 2019; Moscow, Russian Federation.

(Continued)

*Primary Examiner* — C Melissa Koslow
(74) *Attorney, Agent, or Firm* — Stevens & Showalter, L.L.P.

(57) ABSTRACT

The invention relates to faceted gemstones based on a luminescent glass composition that contains particular oxides of rare earth metals and thus enables the faceted gemstones to be identified, and to a process for identifying the gemstones.

10 Claims, 6 Drawing Sheets

(56) References Cited

FOREIGN PATENT DOCUMENTS

RU    2426488 C1    8/2011
RU    2436746 C2    12/2011

OTHER PUBLICATIONS

Appen A.A.; Chemistry of Glass; Khimiya Publishing House; Leningrad Division; 1970; p. 226.
First Office Action; Chinese patent application No. 201580033080.3; dated Feb. 1, 2019; State Intellectual Property Office of the People's Republic of China; Beijing, ROC.
K. Martinek; European Search Report; European Patent Application No. 14182551.3; dated Feb. 10, 2015; European Patent Office: Munich, Germany.

\* cited by examiner

LUMINESCENT GLASS COMPOSITION

CROSS REFERENCE TO RELATED APPLICATIONS

This application is the national stage entry of International Patent Application No. PCT/EP2015/069382 having a filing date of Aug. 24, 2015, which claims priority to and the benefit of European Patent Application No. 14182551.3 filed in the European Patent Office on Aug. 27, 2014, the entire contents of which are incorporated herein by reference,

FIELD OF THE INVENTION

The invention relates to faceted gemstones based on a luminescent glass composition that contains particular oxides of rare earth metals and thus enables the faceted gemstones to be identified, and to a process for identifying the gemstones.

BACKGROUND ART

Synthetic gemstones made of lead-free and lead-containing glass and synthetic precious stones are usually fabricated in completely different qualities. In many countries, gemstones are subject to so-called product compliance guidelines, which limit the content of possibly harmful components.

On the gemstone sector, there has been a strong competition with a massive price pressure in the world market since about 2005. Brand products are often copied, or traded under false statements of origin. Because of the enormous variety of the traded stones, a quick distinction between original and copy is very difficult. The damage caused by trademark counterfeiting is enormous. In addition, the gemstone copies often do not meet the same quality standards and compliance regulations; depending on the country, harmful components may lead to enormous liability problems.

At present, it is common to check the authenticity of synthetic gemstones in accordingly specialized laboratories. For this purpose, the chemical composition of the glass of the gemstone is determined, and its grinding geometry/brilliance is analyzed and compared. Such tests are relatively expensive and time-consuming and cannot be employed for a quick analysis on the market.

A known method for identifying synthetic gemstones is labeling with laser engraving. Because of its high cost and technical limits, this method can be employed for synthetic gemstones of glass only to a very limited extent.

In order to protect luxury products from trademark counterfeiting, numerous product authentication solutions exist, such as multistage safety stickers, holograms, safety inks, RFID (radio frequency identification) systems, etc. However, these methods are not applicable to gemstones, because they would adversely affect the optical appearance of the gemstone.

A combination of luminescent markers that can be applied to or introduced in articles is known from WO 2011/141461 A1 (Uni Berlin). These luminescent markers cannot be molten into the glass with preservation of the chemical bonds. Rather, the original chemical compounds that were the components of the luminescent markers are dissolved in the glass network after the melting. The original luminescence of the ceramic particles according to the patent is lost and therefore can no longer be detected in the finished products.

Luminescent phosphorous glasses that contain more than 2 mole percent of particular oxides of rare earth metals are known from patent specification US 2005 0253113 (Schott). Quartz glasses doped with rare earth elements are known from EP 0 466 932 A1 (Furukawa).

Glass beads containing dopants selected from rare earths in amounts of 0.5 to 3 mole percent are known from U.S. Pat. No. 7,256,398. However, dopants are undesirable in glass in such relatively high concentrations, because rare earths are known to change the color of the glass. In addition, dopants added in the above mentioned concentrations lead to significant increases of the raw material cost of the glass mixture, so that such compositions can no longer be employed in an economically efficient way for synthetic gemstones.

Dopants in concentrations of one-digit percentages (1% corresponds to 10,000 mg/kg) can be detected relatively simply with common analytical methods, such as RFA. However, they lead to colorings of the glasses and therefore are not suitable as dopants in such concentrations.

It is the object of the present invention to provide faceted gemstones of glass that are luminescent, but contain so small amounts of dopants that they do not cause color changes in the glass on the one hand, but have clearly identifiable bands in the emission spectrum on the other. The dopants serve as "markers of authenticity" and enable identification through a portable analytical device.

DESCRIPTION OF THE INVENTION

Surprisingly, it has been found that this object can be achieved by faceted gemstones of glass according to the present invention. The oxides of the rare earth metals scandium, lanthanum, cerium, praseodymium, samarium, europium, yttrium, terbium, dysprosium, holmium, thulium, ytterbium and lutetium are contained in these compositions in concentrations of from 2 to 2000 mg/kg of the glass composition (corresponding to 0.0002 to 0.2% by weight, based on one kilogram of the glass composition) and provide for a sufficiently strong fluorescence radiation that enables identification even at such low concentrations (cf. FIGS. 1 to 4). A preferred embodiment of the glass composition contains the specific oxides of the rare earth metals in about 5 to about 1000 mg/kg of the glass composition; particularly preferred are concentrations of about 5 to about 700 mg/kg and, in particular, about 5 to about 500 mg/kg, even more preferably about 5 to about 300 mg/kg.

Upon excitation with light, especially in the visible range, the gemstones of glass faceted according to the present invention show characteristic fluorescent signals for markers and crystal glass matrix, which can be read out with corresponding devices. Preferably, at least two, more preferably at least three, different oxides of the mentioned rare earth metals are contained in the gemstones of glass faceted according to the invention. This enables the fluorescence emission spectrum to be used as a "finger print" for identifying the glass composition. In addition, varying the concentration ratios of the oxides of the rare earth metals in the individual batches during the glass production and integrating the intensities of the peaks enables not only an authenticity check, but also assignment to batches, i.e., the production date can also be determined.

Because of the particular reflection properties, which are due to the faceting of gemstones, it is possible to recognize very low contents of marker elements by means of miniaturized high performance spectrometers, even if comparably small gemstones are incorporated in jewels. The reason for this effect resides in the mostly multiple reflection of light beams in faceted gemstones, which results in a long traveling path or a high probability of excitation. A quantitative analysis of the underlying glass composition and especially of the dopants would not be possible at such low concentrations, or only so at a very high expenditure. The methods of obtaining facetings (e.g., by grinding and polishing or blank pressing) are sufficiently known to the skilled person.

Facetted gemstones according to the invention based on doped glass compositions are available, for example, from Swarovski under the designations A 5328 MM2.5 Cry, A 5000 MM10 Cry, A 6041 MM18 Cry.

In addition, especially when facetted gemstones are mirrored ("foiling"), an exit of fluorescent signals into the direction of the viewer is favored. Therefore, facetted gemstones of glass that are partially mirrored are particularly preferred according to the invention. "Partially mirrored" means that at least one facet or face is mirrored. For example, in chatons, the pavilion faces are mirrored. The mirroring and the methods for mirroring are sufficiently known to the skilled person (see below). Facetted and mirrored gemstones according to the invention are available, for example, from Swarovski under the designations A 1100 PPO Cry F (F represents foiled; silver mirror), A 1088 SS39 Cry F, A 2058 SS6 Cry F, A 2088 SS34 Cry F, A 2078 SS6 Cry A HF (A representing an alternative silver mirror), A 2078 SS6 Cry M HF (M representing Al mirrors).

By combining different marker elements in variable concentration ratios, some kind of interior coding of the crystal glass products marked in this way can be effected as mentioned above. Thus, the proportion of terbium oxide was selected to be 0.015% by weight, and that of dysprosium oxide to be 0.006% by weight, in Example 2 (Table 1).

Because of the faceting of the glass gemstones and the thereby increased reflection as compared to non-ground glass pieces, extremely low concentrations of the dopants can be employed (see above), even within a range of from 5 to 300 mg/kg.

Excitation and Detection

The detection of the labeling is effected with portable optical analytical devices, which excite the facetted gemstones with electromagnetic radiation in selected wavelength ranges. The fluorescence emission radiation, and optionally its decay behavior, is subsequently read out in a wavelength-selective way and analyzed by using suitable algorithms in order to recognize the authenticity of the gemstone. Such analytical devices are prepared and sold, for example, by the company Swiss Authentication Research and Development AG. The wavelength-selective evaluation enables a quantitative comparison of the fluorescence signals at the respectively characteristic wavelengths of the admixed rare earth metal oxides. According to the invention, it is preferred to employ faceted gemstones made of glass that exhibit a fluorescence within a range of 300 to 3000 nm, preferably within a range of 300 to 1100 nm, upon excitation by electromagnetic radiation.

The invention also relates to a process for identifying a faceted gemstone made of glass, comprising the following steps:
  (a) providing a faceted gemstone made of glass according to the invention;
  (b) exciting it with electromagnetic radiation;
  (c) detecting the generated fluorescence; and
  (d) optionally comparing the signal with a given pattern.

Preferably, the excitation is effected in a wavelength-selective way, more preferably at wavelengths of 300 to 780 nm. In a preferred embodiment, the process serves for the identification of the production batch of the faceted gemstone made of glass.

Glass Composition

The invention is not limited in principle with respect to the composition of the glass from which the faceted gemstone is prepared. "Glass" means a frozen supercooled liquid that forms an amorphous solid. According to the invention, both doped oxidic glasses and chalcogenide glasses, metallic glasses or non-metallic glasses can be employed. Oxynitride glasses may also be suitable. The glasses may be one-component (e.g., quartz glass) or two-component (e.g., alkali borate glass) or multicomponent (soda lime glass) glasses.

The doped glass composition of the faceted gemstones according to the invention can be prepared by melting, by sol-gel processes, or by shock waves. The methods are known to the skilled person. Inorganic glasses, especially oxidic glasses, are preferred according to the invention. These include silicate glasses, borate glasses or phosphate glasses. Lead-free glasses are particularly preferred. For the preparation of faceted gemstones, silicate glasses are preferred. Silicate glasses have in common that their network is mainly formed by silicon dioxide ($SiO_2$). By adding further oxides, such as alumina or various alkali oxides, alumosilicate or alkali silicate glasses are formed. For the classification, it is critical which oxide is the second most abundant in the silicate base glass in terms of quantity. A silicate glass without further components, i.e., pure $SiO_2$, is referred to as silica or quartz glass. If phosphorus pentoxide or boron trioxide are the main network formers of a glass, it is referred to as a phosphate or borate glass, respectively, whose properties can also be adjusted by adding further oxides. The mentioned glasses mainly consist of oxides, which is why they are generically referred to as oxidic glasses.

In a preferred embodiment, the doped glass composition contains the following components in addition to the oxides of the rare earth metals scandium, lanthanum, cerium, praseodymium, samarium, europium, yttrium, terbium, dysprosium, holmium, thulium, ytterbium and lutetium in the amounts according to the claims:
  (a) about 35 to about 85% by weight $SiO_2$;
  (b) 0 to about 20% by weight $K_2O$;
  (c) 0 to about 20% by weight $Na_2O$;
  (d) 0 to about 5% by weight $Li_2O$;
  (e) 0 to about 13% by weight ZnO;
  (f) 0 to about 11% by weight CaO;
  (g) 0 to about 7% by weight MgO;
  (h) 0 to about 10% by weight BaO;
  (i) 0 to about 4% by weight $Al_2O_3$;
  (j) 0 to about 5% by weight $ZrO_2$;
  (k) 0 to about 6% by weight $B_2O_3$;
  (l) 0 to about 3% by weight F;
  (m) 0 to about 2.5% by weight Cl.
Preferably, the doped glass composition contains:
  (a) about 45 to about 75% by weight $SiO_2$;
  (b) 0 to about 10% by weight $K_2O$;
  (c) about 5 to about 20% by weight $Na_2O$;
  (d) about 0.5 to about 5% by weight $Li_2O$;
  (e) about 3 to about 13% by weight ZnO;
  (f) about 2 to about 11% by weight CaO;
  (g) 0 to about 7% by weight MgO;

(h) 0 to about 10% by weight BaO;
(i) about 0.5 to about 4% by weight $Al_2O_3$;
(j) about 0.5 to about 4% by weight $ZrO_2$;
(k) about 1 to about 6% by weight $B_2O_3$;
(l) 0 to about 3% by weight F;
(m) 0 to about 2.5% by weight Cl.

Particularly preferred according to the invention is a glass composition containing:
(a) about 48 to about 65% by weight $SiO_2$;
(b) about 1 to about 5% by weight $K_2O$;
(c) about 10 to about 17% by weight $Na_2O$;
(d) about 0.5 to about 3% by weight $Li_2O$;
(e) about 7 to about 13% by weight ZnO;
(f) about 4 to about 11% by weight CaO;
(g) 0 to about 3% by weight MgO;
(h) 0 to about 1% by weight BaO;
(i) about 0.5 to about 4% by weight $Al_2O_3$;
(j) about 0.5 to 4% by weight $ZrO_2$;
(k) about 3 to about 6% by weight $B_2O_3$;
(l) 0 to about 3% by weight F;
(m) 0 to about 2.5% by weight Cl.

In another preferred embodiment based on borosilicate glass, the doped glass composition contains the following components in addition to the dopants according to the claims at a concentration according to the claims:
(a) about 30 to about 95% by weight $B_2O_3$;
(b) 0 to about 20% by weight $K_2O$;
(c) 0 to about 25% by weight $Na_2O$;
(d) 0 to about 5% by weight $Li_2O$;
(e) 0 to about 13% by weight ZnO;
(f) 0 to about 11% by weight CaO;
(g) 0 to about 7% by weight MgO;
(h) 0 to about 10% by weight BaO;
(i) 0 to about 4% by weight $Al_2O_3$;
(j) 0 to about 5% by weight $ZrO_2$;
(k) 0 to about 3% by weight F;
(l) 0 to about 2.5% by weight Cl.

In another preferred embodiment based on phosphate glass, the doped glass composition contains the following components in addition to the dopants according to the claims at a concentration according to the claims:
(a) about 30 to about 95% by weight $P_2O_5$;
(b) 0 to about 30% by weight $K_2O$;
(c) 0 to about 30% by weight $Na_2O$;
(d) 0 to about 10% by weight $Li_2O$;
(e) 0 to about 20% by weight ZnO;
(f) 0 to about 20% by weight CaO;
(g) 0 to about 15% by weight MgO;
(h) 0 to about 30% by weight BaO;
(i) 0 to about 15% by weight $Al_2O_3$;
(j) 0 to about 15% by weight $SiO_2$;
(k) 0 to about 15% by weight $B_2O_3$;
(l) 0 to about 20% by weight BaO.

All stated amounts are to be understood as giving a total sum of 100% by weight.

Glass Coating (Foiling or Mirroring)

Coatings usually contain a layer of a metal and/or a metal compound, such as metal oxides, metal nitrides, metal fluorides, metal carbides, or any combination of such compounds in any order, which are applied to the faceted gemstones by means of one of the usual coating methods. Also, successive layers of different metals or metal compounds may be applied. The methods and coatings are sufficiently known to the skilled person.

The mirroring methods include, inter alia, PVD (physical vapor deposition), CVD (chemical vapor deposition), paint-coating methods and wet chemical methods according to the prior art.

General Principle of Measurement for the Fluorescence Spectra

Suitable measuring devices are sold by the company Horiba Jobin Yvon GmbH, inter alia. In such measuring devices, the radiation emitted by one or more light sources of different wavelength ranges is broken up spectrally and selected through an arrangement of optical elements and aperture slots. The radiation spectrally limited in kind is converged by beam shaping elements and guided onto the object to be measured. If an emission occurs because of the above mentioned irradiation of the sample object, it exits into the sample chamber surrounding the measuring object. Through an optical set-up (detector set-up) upstream of the detector, the emitted radiation is again broken up spectrally and geometrically oriented towards the detector. This can be done by means of a mirror system both under a right angle to the excitation radiation and under a small angle to the normal of the excitation radiation. The detector set-up essentially consists of an array of light-sensitive sensors. By the above described geometric adjustment of the spectrally dispersed radiation onto the array of detector elements, wavelength ranges can be assigned to the individual sensors. The read-out system contains a programmable electronic unit which enables the received signals to be processed and digitally evaluated. The measuring signal obtained can thus be processed digitally and stored.

Measuring Principle for Portable Detectors

Suitable devices are sold by the company Swiss Authentication Research and Development AG (see above). The radiation emitted by one or more light sources is guided through an arrangement of optical beam shaping elements onto the object to be measured. If an emission occurs because of the above mentioned irradiation of the sample object, it is collected by an arrangement of optical elements and directed onto an optical grid. The radiation spectrally dispersed in this way is projected onto a detector array, so that wavelength ranges are assigned to the individual sensors. The read-out system contains a programmable electronic unit which enables the received signals to be processed and digitally evaluated. The measuring signal obtained can thus be processed digitally and stored.

Faceted stones (cuboid of dimensions 40 mm×12 mm×12 mm) made of the glass compositions of Table 1 all show a fluorescence spectrum that allows for an unequivocal identification (cf. FIGS. 1-4), in addition to the typical emission of the respective glass matrix (glass fluorescence), which is found in different ranges for the different glasses. In the following, the spectra of Examples 1, 2 and 3 according to the invention are depicted by way of example. It is to be noted that the excitation radiation scattered in the sample chamber of the measuring device is also depicted in the Figures. It is visible as the first and second order of the scattered excitation radiation. By way of example for 1, the excitation can be seen at 471 nm (first order) and 942 nm (second order). Therefore, the peaks at these wavelengths are measuring artifacts and can be neglected.

Simulation of Fluorescence Emission

Figure 5:
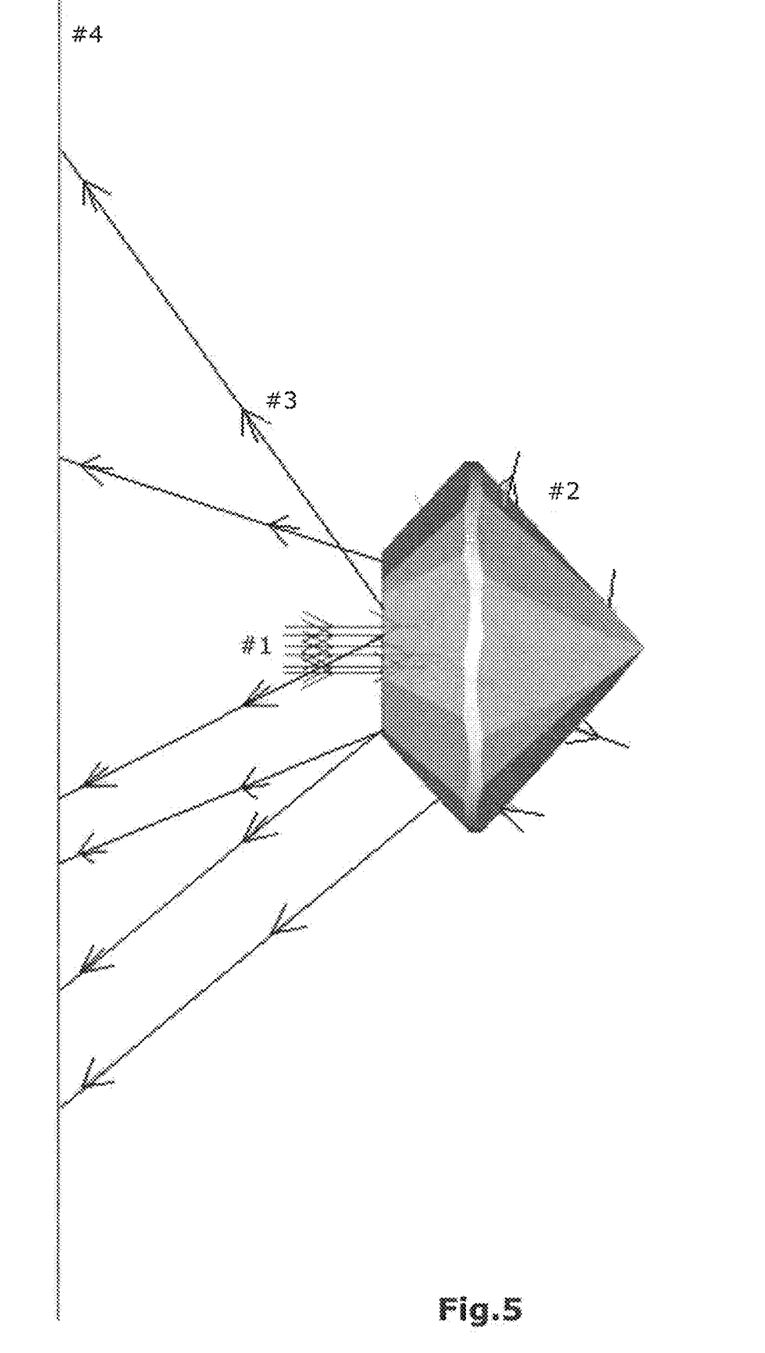
FIG. 5: Schematic representation of the simulation set-up with the following legend:
1 light source with collimated beams of wavelength 450 nm;
2 chaton geometry;
3 fluorescence emission at 650 nm;
4 detector.

In order to compare the fluorescence emissions of non-faceted and faceted glass and to examine the effects of mirroring of the faceted glass stones, simulations of fluorescence emission were performed by means of the ray tracing software Zemax of the company Radiant Zemax (set-up cf. FIG. 5).

Three different fluorescence emissions were simulated:
(i) for a glass bead of 4 mm radius and the parameters for Schott-N-BK7® glass as present in the program; 2.2 mm distance from the light source;
(ii) for a Xilion 1028 SS39 chaton of the company Swarovski with a diameter of 8.3 mm and a total length of 5.8 mm and the parameters for Schott-N-BK7® glass as present in the program; 2.2 mm distance from the light source; table face of the chaton vertical to the propagation direction of the light;
(iii) for the chaton corresponding to b) whose pavilion facets were simulated to be mirrored (i.e., pavilion facets were assumed to be totally reflecting).

In the simulation, the light source was assumed to be perfectly collimated with a total power of 1 Watt, a radius of 1 mm and an emitted wavelength of 450 nm. In the simulation, the light source was positioned in such a way that the incidence of the light beams onto the objects was perpendicular to the tangential plane of the point of entry (in the case of the bead) or perpendicular to the table plane and through the circumcenter of the table (in the case of the chaton).

Through the parameter "free path", it was defined how far the impinging beams will penetrate into the glass object before they are absorbed and then emitted in the form of fluorescence radiation (650 nm). This corresponds to a simulation of different concentrations of dopant in the glass composition. The shorter the free path, the higher is the concentration of dopant; the longer the free path, the lower is the concentration of dopant.

In the simulation, a rectangle of the area 30 mm×30 mm served as a detector for the fluorescent emission and was placed at a distance of −5 mm (i.e., 5 mm behind the light source; cf. FIG. 5) from the light source vertically to the beam axis of the light source and recorded only the emitted radiation (650 nm).

The beams impinging on the respective glass object a) to c) were subject to Snell's refraction and reflection. The radiation of wavelength 450 nm originating from the light source was emitted by the glass bodies as a fluorescence radiation of wave-length 650 nm to different extents.

Figure 6:
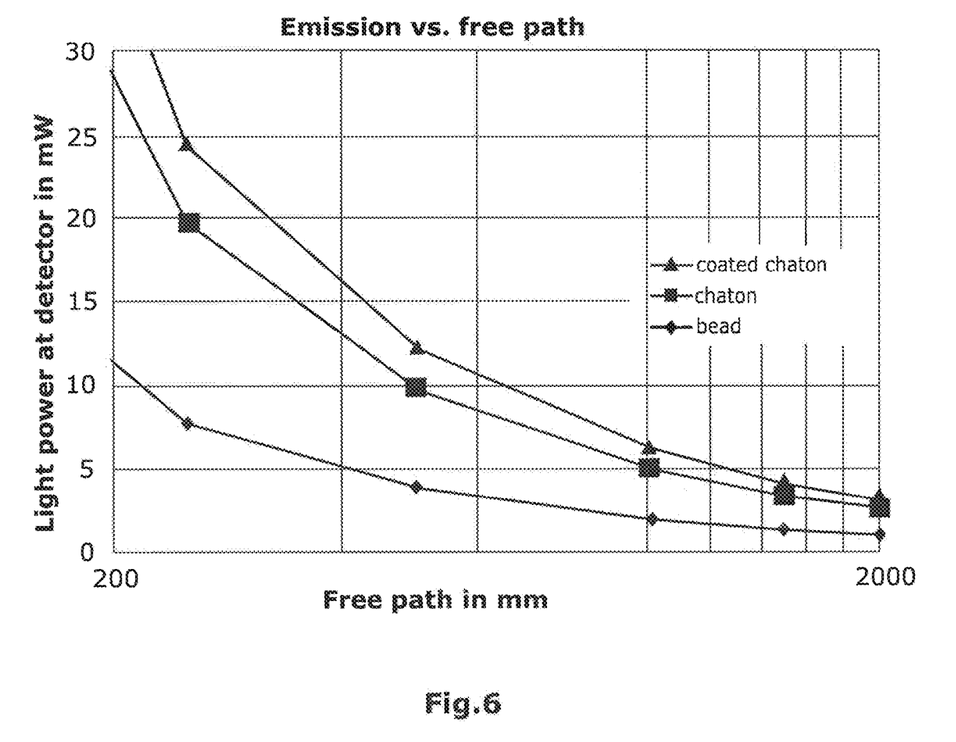
FIG. 6: Simulation of fluorescence emission as a function of geometry and free path.

The light powers impinging on the detector for the three different geometries were compared. The simulations (FIG. 6) show clearly that the least fluorescence emission occurs in the case of a spherical geometry (a). The fluorescence emission of the Xilion 1028 chaton SS39 is more than twice as high over the whole range of free paths; this corresponds to an increase of fluorescence of more than 100% as compared to a non-faceted glass body. A coated/mirrored chaton shows a further increase of the fluorescence emission, albeit less significant.

EXAMPLES

Examples 1 to 15

Figure 1:
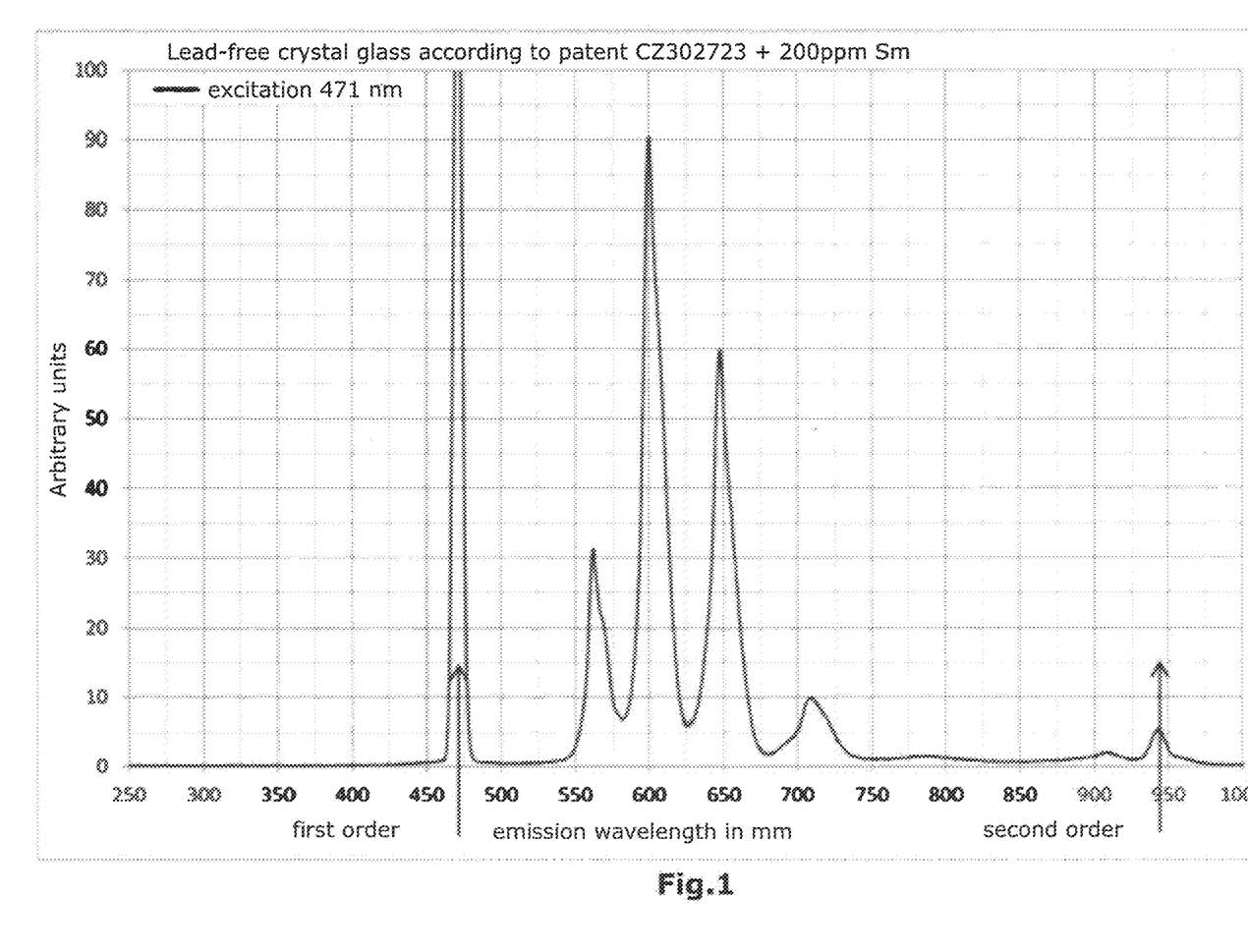
FIG. 1: Measured fluorescence emission of a lead-free crystal glass according to Example 1 with 200 ppm $Sm_2O_3$ additive (excitation at 471 nm), measured on a cuboid of the size 40 mm×12 mm×12 mm.
Figure 2:
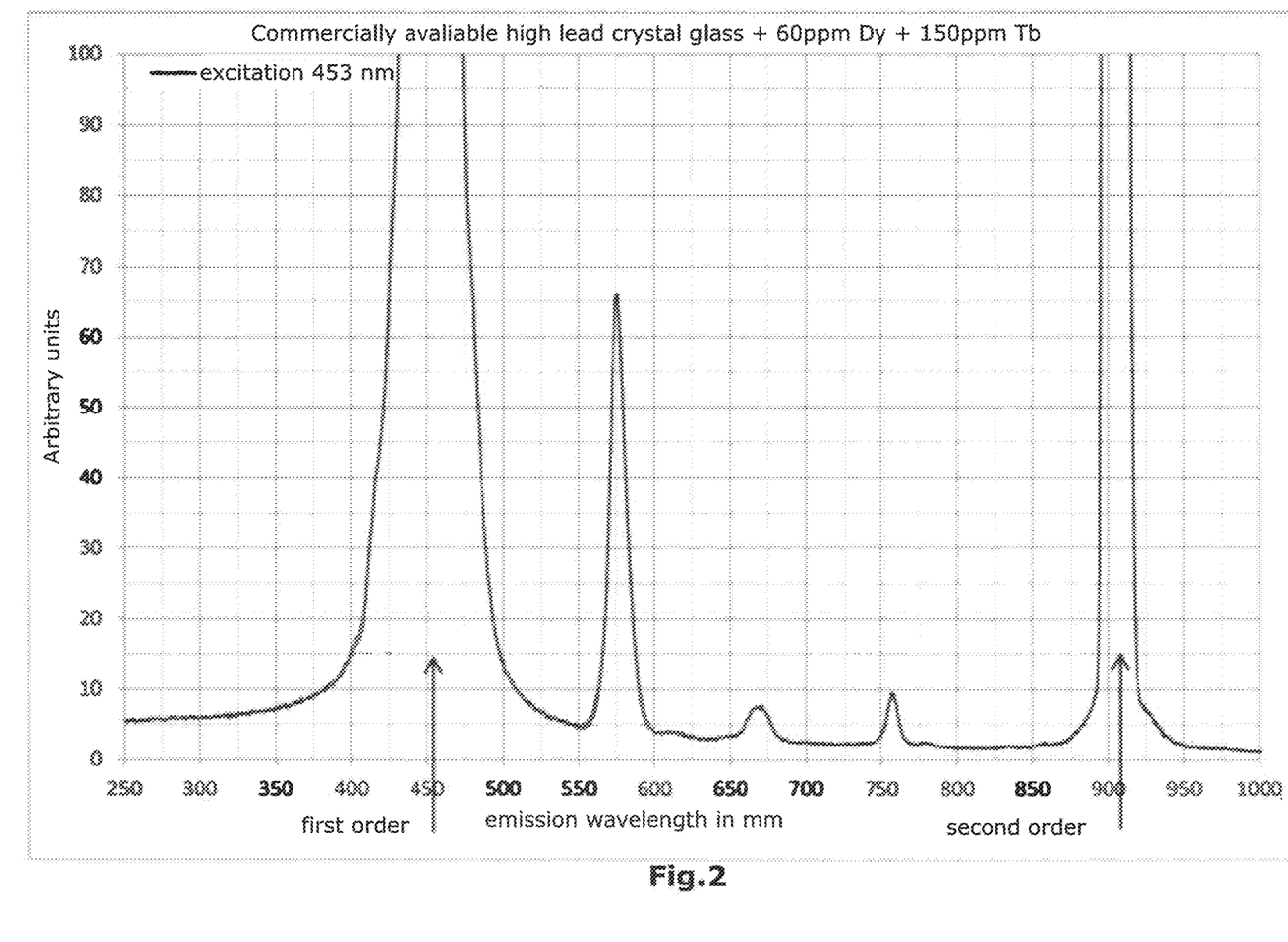
FIG. 2: Measured fluorescence emission of a high lead crystal glass according to Example 2 with 60 ppm $Dy_2O_3$ and 150 ppm $Tb_2O_3$ additives (excitation at 453 nm), measured on a cuboid of the size 40 mm×12 mm×12 mm.
Figure 3:
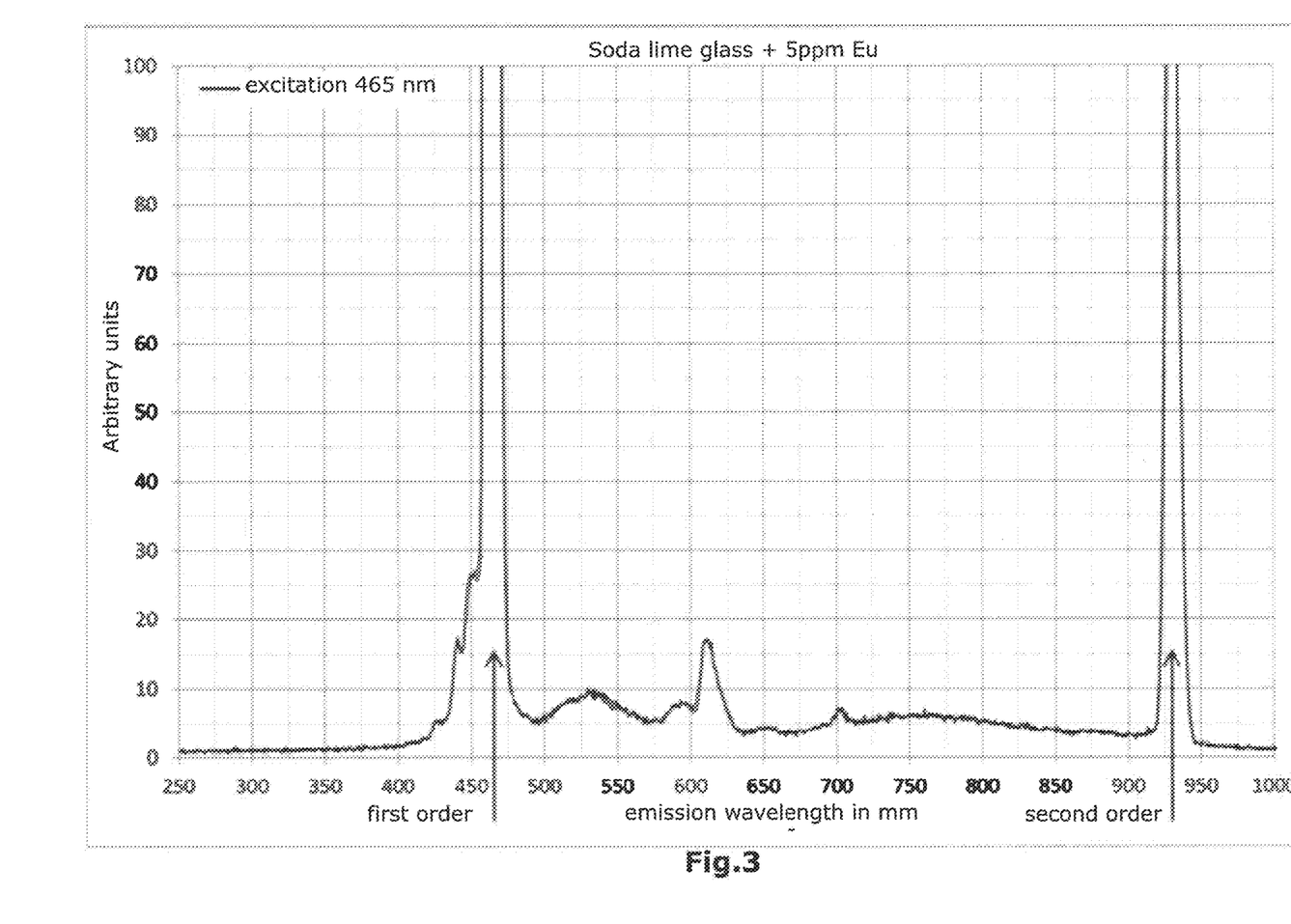
FIG. 3: Measured fluorescence emission of a soda lime glass according to Example 3 with 5 ppm $Eu_2O_3$ additive (excitation at 465 nm), measured on a cuboid of the size 40 mm×12 mm×12 mm.
Figure 4:
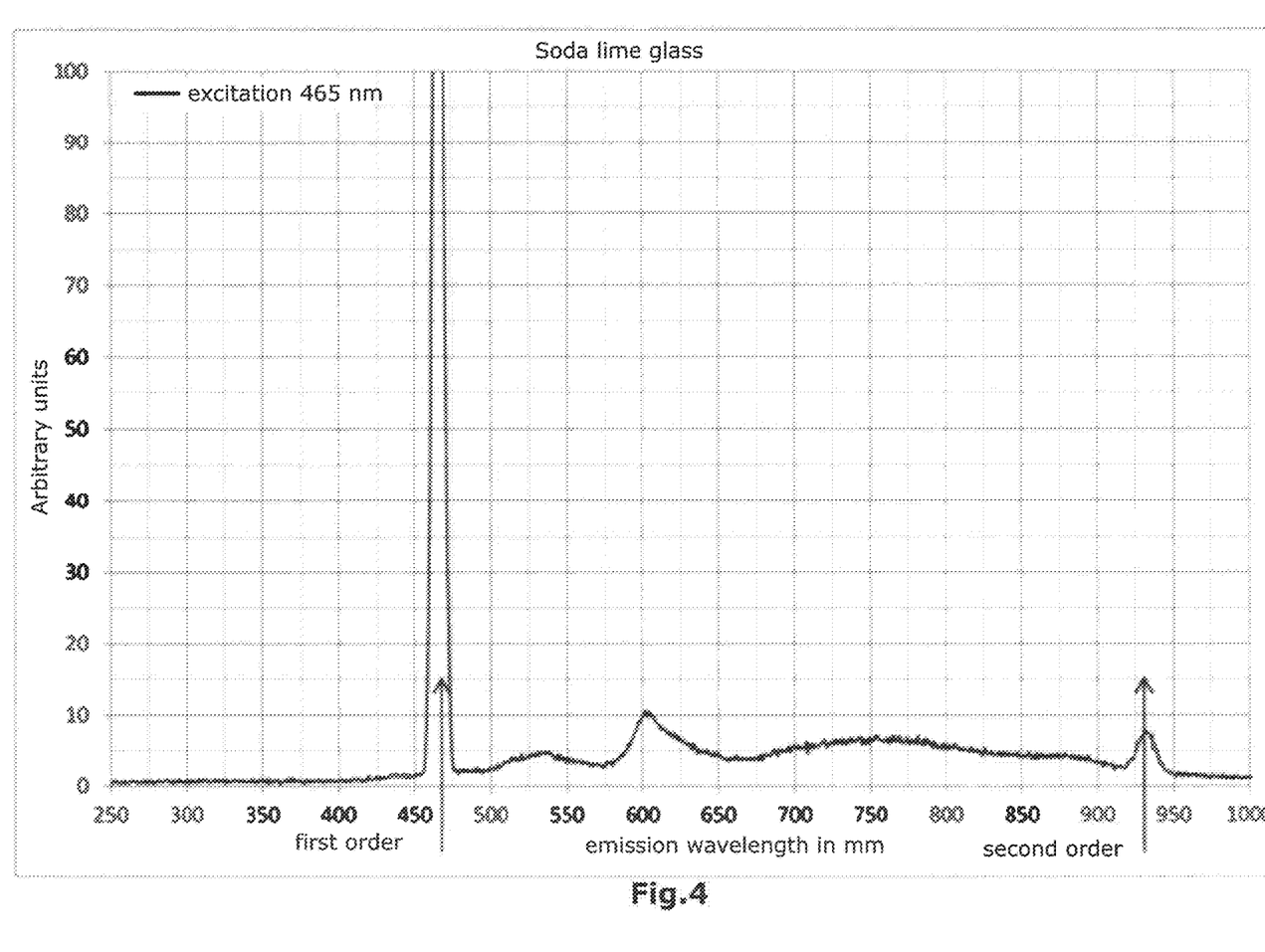
FIG. 4 (Comparative Example): Measured fluorescence emission of a soda lime glass without dopant addition (excitation at 465 nm), measured on a cuboid of the size 40 mm×12 mm×12 mm.

The following Table 1 represents the oxide compositions of different glasses used for the preparation of the faceted gemstones. All amounts are stated as percentages by weight. The Examples relate to the following glasses:

Example 1: lead-free crystal glass according to patent CZ302723 (cf. FIG. 1); Example 2: commercially available high lead crystal glass (cf. FIG. 2); Example 3: commercially available soda lime glass (cf. FIG. 3); Example 4: standard optical glass N-BK7®; Example 5: commercially available borosilicate glass; Examples 6 to 15: commercially available colored glasses.

All glasses contain the dopants in the amounts according to the invention.

TABLE 1

| Glass compositions with dopants (Part 1) | | | | | | | |
|---|---|---|---|---|---|---|---|
| Example | 1 | 2 | 3 | 4 | 5 | 6 | 7 |
| $SiO_2$ | 59.11 | 55.25 | 72.69 | 70.30 | 80.24 | 72.28 | 70.30 |
| PbO | | 31.90 | | | | | |
| $K_2O$ | 3.49 | 8.80 | | 7.70 | 0.20 | 4.00 | 5.90 |
| $Na_2O$ | 11.40 | 2.30 | 13.20 | 10.24 | 4.60 | 15.00 | 10.60 |
| $B_2O_3$ | 3.07 | 0.30 | | 10.00 | 12.60 | | |
| $Li_2O$ | 2.15 | | | | | | |
| CaO | 7.19 | | 9.29 | 0.20 | | 2.90 | 6.70 |
| MgO | | | 3.80 | | | | |
| ZnO | 7.71 | 1.00 | | | | | 1.10 |
| $Al_2O_3$ | 0.43 | | 0.70 | | 2.30 | 0.10 | 1.60 |
| $TiO_2$ | 2.08 | | | 0.20 | | 4.00 | |
| $As_2O_3$ | | | | | | | |
| $Sb_2O_3$ | 0.47 | 0.43 | 0.32 | 0.26 | | 0.12 | 0.50 |
| BaO | | | | 0.90 | | 1.50 | |
| $ZrO_2$ | 2.08 | | | | | | |

TABLE 1-continued

| | | | | | | | |
|---|---|---|---|---|---|---|---|
| $P_2O_5$ | 0.70 | | | | | | |
| $Gd_2O_3$ | 0.10 | | | | | | |
| $Nd_2O_3$ | | | | | | | 1.30 |
| $SnO_2$ | | | | | | | 1.90 |
| $Sm_2O_3$ | 0.0200 | | — | | | 0.0300 | |
| $Eu_2O_3$ | | | 0.0005 | | 0.0050 | | |
| $Ho_2O_3$ | | | — | 0.1700 | 0.0500 | | |
| $Tb_4O_7$ | | 0.0150 | | 0.0300 | | | 0.0300 |
| $Dy_2O_3$ | | 0.0060 | | | 0.0100 | | |
| $Sc_2O_3$ | | | | | | 0.0400 | |
| CeO | | | | | | | 0.0400 |
| $Yb_2O_3$ | | | | | | | 0.0300 |
| $Lu_2O_3$ | | | | | 0.0300 | | |

Glass compositions with dopants (Part 2)

| Example | 8 | 9 | 10 | 11 | 12 | 13 | 14 | 15 |
|---|---|---|---|---|---|---|---|---|
| $SiO_2$ | 73.00 | 69.10 | 65.29 | 64.94 | 65.73 | 70.57 | 71.93 | 73.80 |
| PbO | | | 0.90 | | | | | |
| $K_2O$ | 7.50 | 11.00 | 4.70 | 2.20 | | 2.60 | 0.70 | |
| $Na_2O$ | 12.00 | 8.00 | 8.40 | 20.80 | 19.30 | 17.20 | 15.20 | 10.90 |
| $B_2O_3$ | 2.00 | | | 3.80 | 4.10 | 2.40 | | 1.00 |
| CaO | 2.80 | 7.00 | 6.40 | 4.80 | 4.20 | 3.30 | 5.30 | 7.00 |
| MgO | | | 2.70 | 0.20 | 0.10 | 0.20 | 0.10 | 0.20 |
| ZnO | | 3.00 | | 1.70 | | 0.70 | | |
| $Al_2O_3$ | 2.00 | 1.00 | 0.10 | 0.20 | 2.70 | 1.70 | 4.90 | 6.80 |
| $As_2O_3$ | | | | | | 0.70 | | |
| $Sb_2O_3$ | 0.30 | 0.30 | 0.30 | | | | | 0.18 |
| BaO | 0.30 | 0.50 | 11.00 | | | | | |
| SrO | | | 0.10 | | | | | |
| $P_2O_5$ | | | | | 3.80 | | | |
| F | | | | 1.30 | | 0.50 | | |
| $Er_2O_3$ | | | | | | | 1.80 | |
| $Sm_2O_3$ | | | | 0.0100 | | | | 0.0300 |
| $Eu_2O_3$ | 0.0300 | | | 0.0200 | | | 0.0250 | 0.0200 |
| $Ho_2O_3$ | 0.0200 | | | | | | 0.0125 | 0.0100 |
| $Tb_4O_7$ | | | | | 0.0300 | | | |
| $Dy_2O_3$ | | 0.0300 | 0.0300 | 0.0200 | | 0.0300 | | |
| $Sc_2O_3$ | | | 0.0200 | | | 0.0500 | | 0.0100 |
| $Y_2O_3$ | 0.0200 | | 0.0100 | 0.0100 | | | | |
| $La_2O_3$ | | 0.0400 | | | 0.0150 | | | |
| CeO | | | | | | | 0.0125 | |
| $Pr_6O_{11}$ | 0.0300 | | | | | 0.0200 | | |
| $Tm_2O_3$ | | | 0.0200 | | 0.0300 | | | 0.0200 |
| $Yb_2O_3$ | | 0.0300 | | | | 0.0300 | 0.0250 | 0.0300 |
| $Lu_2O_3$ | | | 0.0300 | | | | | |

The invention claimed is:

1. A faceted gemstone of glass containing at least one dopant selected from the group of oxides of the rare earth metals scandium, lanthanum, cerium, praseodymium, samarium, europium, yttrium, terbium, dysprosium, holmium, thulium, ytterbium and lutetium, characterized in that the total amount of the oxides of rare earth metals is 2-2000 mg/kg of the glass composition, said glass comprising the following components:
 (a) 35 to 85% by weight $SiO_2$;
 (b) 0 to 20% by weight $K_2O$;
 (c) 0 to 20% by weight $Na_2O$;
 (d) 0 to 5% by weight $Li_2O$;
 (e) 0 to 13% by weight ZnO;
 (f) 0 to 11% by weight CaO;
 (g) 0 to 7% by weight MgO;
 (h) 0 to 10% by weight BaO;
 (i) 0 to 4% by weight $Al_2O_3$;
 (j) 0 to 2% by weight $ZrO_2$;
 (k) 0 to 6% by weight $B_2O_3$;
 (l) 0 to 3% by weight F;
 (m) 0 to 2.5% by weight Cl;
 the stated amounts summing up to 100% by weight.

2. The faceted gemstone of glass according to claim 1, characterized in that the total amount of the oxides of rare earth metals is 5-700 mg/kg of the glass composition.

3. The faceted gemstone of glass according to claim 1, characterized in that a mixture of at least two oxides of the rare earth metals is employed.

4. The faceted gemstone of glass according to claim 1, characterized in that said faceted gemstone exhibits a fluorescence within a range of 300 to 3000 nm upon excitation by electromagnetic radiation.

5. The faceted gemstone of glass according to claim 1, wherein the faceted gemstone of glass is partially mirrored.

6. The faceted gemstone of glass according to claim 1, characterized in that a mixture of at least three oxides of the rare earth metals is employed.

7. The faceted gemstone of glass according to claim 1, characterized in that said faceted gemstone exhibits a fluorescence within a range of 300 to 1100 nm upon excitation by electromagnetic radiation.

8. A faceted gemstone of glass containing at least one dopant selected from the group of oxides of the rare earth metals scandium, lanthanum, cerium, praseodymium, samarium, europium, yttrium, terbium, dysprosium, holmium, thulium, ytterbium and lutetium, characterized in that the total amount of the oxides of rare earth metals is 2-2000 mg/kg of the glass composition, said glass comprising the following components:

(a) 30 to 95% by weight $B_2O_3$;
(b) 0 to 20% by weight $K_2O$;
(c) 0 to 25% by weight $Na_2O$;
(d) 0 to 5% by weight $Li_2O$;
(e) 0 to 13% by weight ZnO;
(f) 0 to 11% by weight CaO;
(g) 0 to 7% by weight MgO;
(h) 0 to 10% by weight BaO;
(i) 0 to 4% by weight $Al_2O_3$;
(j) 0 to 5% by weight $ZrO_2$;
(k) 0 to 3% by weight F;
(l) 0 to 2.5% by weight Cl;
the stated amounts summing up to 100% by weight.

9. A faceted gemstone of glass containing at least one dopant selected from the group of oxides of the rare earth metals scandium, lanthanum, cerium, praseodymium, samarium, europium, yttrium, terbium, dysprosium, holmium, thulium, ytterbium and lutetium, characterized in that the total amount of the oxides of rare earth metals is 2-2000 mg/kg of the glass composition, said glass comprising the following components:

(a) 30 to 95% by weight $P_2O_5$;
(b) 0 to 30% by weight $K_2O$;
(c) 0 to 30% by weight $Na_2O$;
(d) 0 to 10% by weight $Li_2O$;
(e) 0 to 20% by weight ZnO;
(f) 0 to 20% by weight CaO;
(g) 0 to 15% by weight MgO;
(h) 0 to 30% by weight BaO;
(i) 0 to 15% by weight $Al_2O_3$;
(j) 0 to 15% by weight $SiO_2$;
(k) 0 to 15% by weight $B_2O_3$;
(l) 0 to 20% by weight BaO;
the stated amounts summing up to 100% by weight.

10. A process for identifying a faceted gemstone made of glass according to claim 1, comprising the following steps:
 (a) providing a faceted gemstone made of glass according to claim 1;
 (b) exciting it with electromagnetic radiation;
 (c) detecting the generated fluorescence; and
 (d) optionally comparing the signal with a given pattern.

* * * * *